United States Patent
Noordhoek et al.

(10) Patent No.: US 8,249,213 B2
(45) Date of Patent: Aug. 21, 2012

(54) CALIBRATION METHOD FOR RING ARTIFACT CORRECTION IN NON-IDEAL ISOCENTRIC 3D ROTATIONAL X-RAY SCANNER SYSTEMS USING A CALIBRATION PHANTOM BASED ROTATION CENTER FINDING ALGORITHM

(75) Inventors: Nicolaas Jan Noordhoek, Breda (NL); Jan Timmer, Best (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 13/058,197

(22) PCT Filed: Aug. 11, 2009

(86) PCT No.: PCT/IB2009/053523
§ 371 (c)(1),
(2), (4) Date: Feb. 9, 2011

(87) PCT Pub. No.: WO2010/018537
PCT Pub. Date: Feb. 18, 2010

(65) Prior Publication Data
US 2011/0135053 A1 Jun. 9, 2011

(30) Foreign Application Priority Data
Aug. 13, 2008 (EP) .................................. 08105032

(51) Int. Cl.
*A61B 6/00* (2006.01)
*G01D 18/00* (2006.01)
(52) U.S. Cl. ................ 378/11; 378/4; 378/207
(58) Field of Classification Search ............ 378/4, 11, 378/207
See application file for complete search history.

(56) References Cited

U.S. PATENT DOCUMENTS 6,048,097 A   4/2000   Heinze
(Continued)

FOREIGN PATENT DOCUMENTS

DE            19936409            3/2001
(Continued)

OTHER PUBLICATIONS

Jens et al., Model Based Scatter Correction for Cone-Beam Computed Tomography, Medical Imaging, Proceedings of SPIE, vol. 5745, 2005, pp. 271-282.*

(Continued)

*Primary Examiner* — Alexander H Taningco

(57) ABSTRACT

The present invention refers to 3D rotational X-ray imaging systems for use in computed tomography (CT) and, more particularly, to a fast, accurate and mathematically robust calibration method for determining the effective center of rotation (I) in not perfectly isocentric 3D rotational C-arm systems and eliminating substantially circular ring artifacts (RA) which arise when using such a CT scanner system for acquiring a set of 2D projection images of an object of interest to be three-dimensionally reconstructed. For this purpose, a C-arm based rotational CT scanner comprising at least one radiation detector (D) having an X-radiation sensitive surface exposed to an X-ray beam emitted by at least one X-ray tube (S), each rotating along a non-ideal circular trajectory ($T_F$, $T_{CD}$) about an object of interest to be three-dimensionally reconstructed from a set of 2D projection images is used for providing geometrical calibration data by scanning a calibration phantom from a plurality of distinct projection directions and calculating, for each projection direction, the 3D positions of the X-ray tube's focal spot and the X-ray detector's center. For approximating the exact 3D position and angular direction of the axis of rotation about which the at least one X-ray tube and the at least one radiation detector rotate, a circular regression technique using a number of mathematically robust least squares fits is applied.

20 Claims, 8 Drawing Sheets

U.S. PATENT DOCUMENTS

| | | | |
|---|---|---|---|
| 6,049,582 A * | 4/2000 | Navab | 378/4 |
| 6,148,058 A | 11/2000 | Dobbs | |
| 6,466,638 B1 * | 10/2002 | Silver et al. | 378/4 |
| 7,016,456 B2 * | 3/2006 | Basu et al. | 378/18 |
| 7,186,023 B2 * | 3/2007 | Morita et al. | 378/207 |
| 7,660,450 B2 * | 2/2010 | Van De Haar et al. | 382/131 |
| 7,860,341 B2 * | 12/2010 | Star-Lack et al. | 382/275 |
| 8,043,003 B2 * | 10/2011 | Vogt et al. | 378/207 |
| 2002/0168053 A1 | 11/2002 | Schomberg | |
| 2003/0063709 A1 * | 4/2003 | Lautenschlager et al. | 378/210 |
| 2005/0084147 A1 | 4/2005 | Groszmann | |
| 2005/0119565 A1 | 6/2005 | Pescatore | |
| 2005/0129168 A1 | 6/2005 | Morita | |

FOREIGN PATENT DOCUMENTS

| | | |
|---|---|---|
| DE | 102005013292 | 10/2006 |
| EP | 0964366 | 12/1999 |
| JP | 2006181252 | 7/2006 |
| WO | WO2008015612 | 2/2008 |

OTHER PUBLICATIONS

Marcel Jirina and Frantisek Hakl, "Study of Undeterministic Methods for data Separation in Physics", Institute of computer Science Academy of Sciences of the Czech Republic, pp. 1-35, 2003.

* cited by examiner

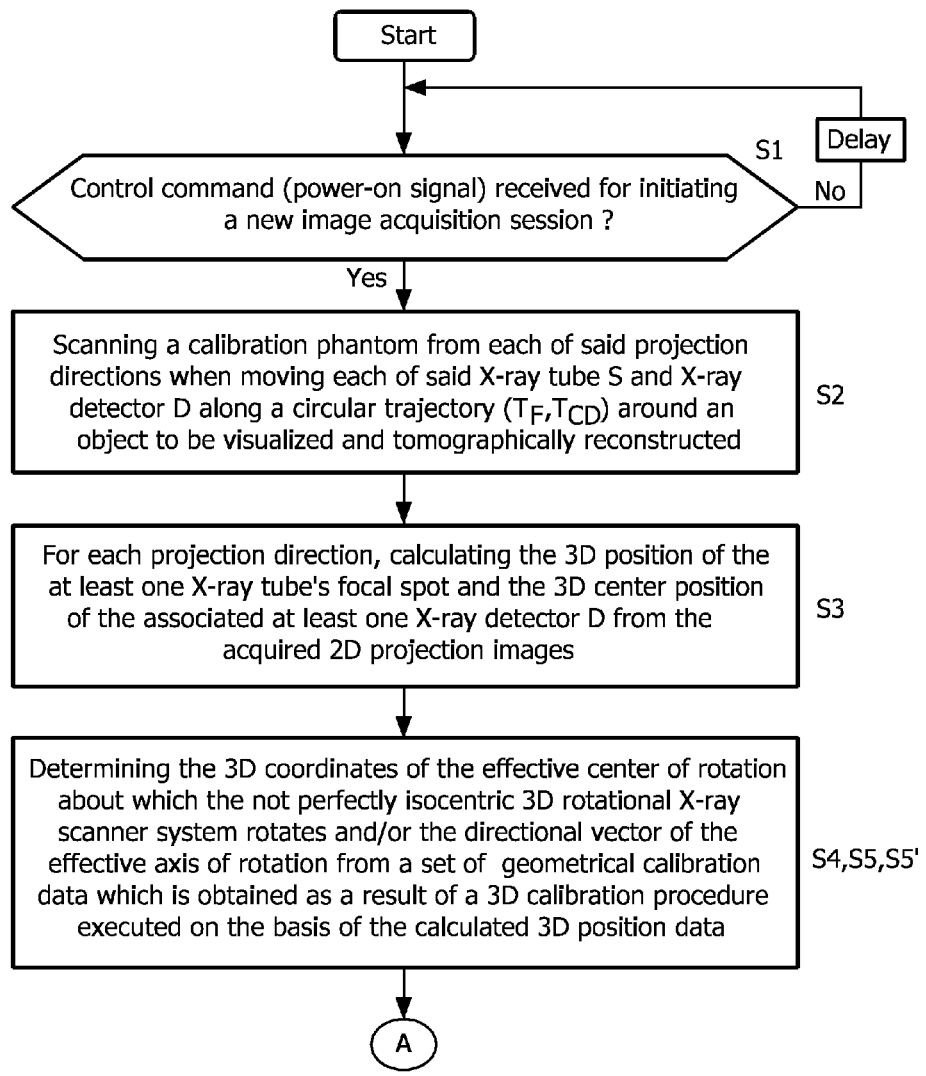
FIG. 5-I

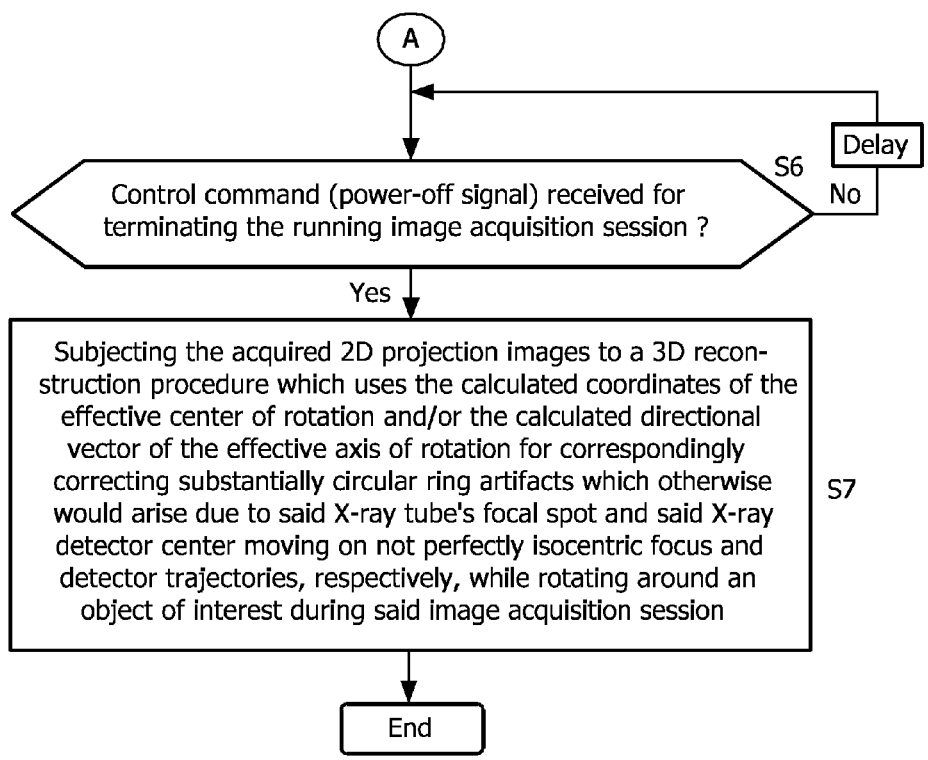
FIG. 5-II

CALIBRATION METHOD FOR RING ARTIFACT CORRECTION IN NON-IDEAL ISOCENTRIC 3D ROTATIONAL X-RAY SCANNER SYSTEMS USING A CALIBRATION PHANTOM BASED ROTATION CENTER FINDING ALGORITHM

FIELD OF THE INVENTION

The present invention refers to 3D rotational X-ray imaging systems for use in computed tomography (CT) and, more particularly, to a fast, accurate and mathematically robust calibration method for determining the effective center of rotation in not perfectly isocentric 3D rotational C-arm systems and eliminating substantially circular ring artifacts which arise when using such a CT scanner system for acquiring a set of 2D projection images of an object of interest to be three-dimensionally reconstructed. For this purpose, a C-arm based rotational CT scanner comprising at least one radiation detector having an X-radiation sensitive surface exposed to an X-ray beam emitted by at least one X-ray tube, each rotating along a non-ideal circular trajectory about an object of interest to be three-dimensionally reconstructed from a set of 2D projection images is used for providing geometrical calibration data by scanning a calibration phantom from a plurality of distinct projection directions and calculating, for each projection direction, the 3D positions of the X-ray tube's focal spot and the X-ray detector's center. For approximating the exact 3D position and angular direction of the axis of rotation about which the at least one X-ray tube and the at least one radiation detector rotate, a circular regression technique using a number of mathematically robust least squares fits is applied.

BACKGROUND OF THE INVENTION

Nowadays, tomographic X-ray imaging technology has found wide acceptance in different fields such as clinical diagnosis, industrial inspection and security screening. In the clinical field, dedicated high-resolution CT imaging systems have recently emerged as important new tools for cancer research, which is because CT scanners are an essential medical image modality to non-invasively examine a region of interest (such as e.g. the interior organs, the cardiovascular system and/or any other anatomical or pathological structures) in the interior of a patient's body. A tomographic imaging system thereby acquires a series of 2D projection images from a number of distinct projection directions around the patient which may then be used for creating a three-dimensional reconstruction of an anatomy to be visualized.

Recently, with use of spiral CT, the new generations of CT scanners, radiologists are able to save much time by rapid examination of a patient during a single breath-hold, thereby utilizing the 3D imaging capability of today's rotational CT imaging systems. In a conventional isocentric 3D rotational X-ray scanner system of the rotary gantry type as used in multi-slice spiral CT, a detector array sensitive to X-radiation is irradiated with a fan- or cone-shaped X-ray beam emitted by an X-ray tube diametrically arranged with respect to said detector array, wherein both said X-ray tube and said detector array are placed on a rotational gantry that is continuously rotated around the patient. To acquire a set of 2D projection images which can be used to reconstruct a three-dimensional image of an anatomy volume in the interior of a patient's body to be non-invasively examined, the X-ray tube and detector array are rotated along a circular trajectory around the patient's body while the patient is lying on a patient table which is advanced along the axis of rotation.

Area-beam detector 3D imaging systems have operated by rotating an X-ray tube and a detector in circular paths around a central axis of rotation. The axis of rotation is positioned to be at the center of a region or volume of interest of a patient anatomy. An X-ray tube and an X-ray detector, such as an image intensifier, are typically mounted at opposite ends of a rotating C-arm support assembly. The X-ray tube irradiates a patient with X-rays that impinge upon a region of interest (ROI) and are attenuated by internal anatomy. The X-rays travel through the patient and are attenuated by the internal anatomy of the patient before the attenuated X-rays then impact the X-ray detector. 3D image data is acquired by taking a series of images while the X-ray tube/C-arm/detector assembly is rotated about the axis of rotation on which the region of interest within the patient is centered. A plurality of two-dimensional (2D) cross-section images are processed and combined to create a 3D image of an object being scanned.

Conventional mobile C-arm assemblies utilize simple support structures and geometries to mount the X-ray tube and X-ray detector on the C-arm. The support structure holds the X-ray tube and detector on the C-arm and maintains a predetermined, constant distance between the X-ray tube and X-ray detector. Thus, the distance between the X-ray tube and the axis of rotation and the distance between the detector and the axis of rotation remain constant and fixed.

In current C-arm X-ray fluoroscopy imaging systems, a 3D tomographic image reconstruction may be performed by sweeping the C-arm in a semi-circular arc around an object of interest. Using cross-arm motion, the arc is circular and therefore isocentric. For example, using a C-arm, an X-ray beam may be swept around a head of a patient (e.g., a CT scan in a circular arc around the head). The volume image reconstruction is performed through 2D projection scan images. Sweeps are accomplished on cross-arm motion with the C-arm positioned at the head of a table sweeping around the head of the table. Thus, the object stays at the center (isocentric motion).

Irrespective of the applied technology, three-dimensionally reconstructed images of an object of interest which are calculated from a set of 2D projection images acquired from a number of distinct projection directions by a rotational CT scanner are often severely distorted by CT artifacts, given by the difference between the detected intensity values in an acquired CT image and the expected attenuation coefficients of the object to be visualized. This is due to multiple reasons which will briefly be explained in the following section. These artifacts, which are still persist in spiral CT as in conventional tomographic X-ray imaging, may enormously degrade the image quality of a reconstructed CT image and play an important role in diagnostic accuracy. Unfortunately, it is not always possible to say if there actually exists an artifact in a CT image because this often depends on a radiologist's judgment. In case of severe artifacts, however, physicians are often not able to give a reliable diagnosis, which is because the anatomies of interest may be hidden or completely distorted.

In general, CT artifacts can be classified into four categories: a) physics-based artifacts including beam hardening, photon starvation and undersampling artifacts, b) patient-based artifacts including metallic and motion artifacts, c) scanner-based artifacts including artifacts which are caused by detector sensitivity and mechanical instability (which is the type of artifacts to which the present invention is dedicated) as well as d) spiral-based artifacts which arise due to spiral interpolation. Careful patient positioning, avoiding patient motion and optimum selection of scanning parameters are thus important factors in avoiding CT artifacts.

The vast majority of artifacts in CT images appears as streak effects and may be caused by metallic objects, beam hardening, photon starvation and/or object motion. If a measurement value of one detector channel in a single reading is disturbed, a single streak occurs. If one channel drops out over a full rotation, which is the case if an X-ray detector of a third-generation rotational CT scanner system is out of calibration, the detector will give a consistently erroneous reading at each angular position, hence resulting in a circular ring artifact.

Another important reason for the emergence of ring artifacts consists in the fact that conventional C-arm based 3D rotational X-ray scanner systems for use in computed tomography that are capable of performing rotational scans for three-dimensionally reconstructing an object of interest, such as e.g. an anatomical region in the interior of a patient's body to be non-invasively examined by means of tomographic X-ray imaging, may not be perfectly isocentric. In practice, mechanical bending and play as well as imperfect aligning of mechanical components may cause the "center of rotation" to vary over the rotation angle. Many conventional C-arm systems in use are unable to perform an exact 3D tomographic reconstruction with an orbital motion of the C-arm because the trajectories of the X-ray tube and detector array may not be perfectly isocentric. As a consequence, acquired 2D projection images of an object of interest to be three-dimensionally reconstructed are distorted due to the non-isocentric imaging arc and are unusable for clinical, diagnostic or interventional purposes. Although circular ring artifacts would rarely be confused with a pathological structure, they can severely impair the diagnostic quality of a tomographic image. For accurate ring artifact detection and correction, it is thus of essential importance that the ring artifact center, which constitutes the effective center of rotation, is known very accurately, which means to a submillimeter level of accuracy down to the 3D volume voxel size, especially for soft tissue imaging. This center position may then be used for eliminating ring artifacts in rendered 3D reconstructions of an object to be visualized. A calibration system and method which improve tomographic image reconstruction by eliminating circular ring artifacts which may arise due to non-isocentric motion of the X-ray tube and detector array when acquiring 2D projection images of an object by means of a not perfectly isocentric 3D rotational X-ray scanner system would hence be highly desirable.

US 2005/0084147 A1 proposes a method for three-dimensionally reconstructing an object of interest based on a set of 2D projection images which are acquired along a non-isocentric trajectory. As described in this document, said method comprises the steps of determining and varying a distance between an object and at least one of an X-ray tube and an X-ray sensitive detector to form a virtual isocenter, maintaining an object at said virtual isocenter during the imaging of said object, normalizing a magnification change in image data obtained while said virtual isocenter is maintained and reconstructing an image of said object based on said image data and said normalized magnification change. The herein disclosed method may further comprise the step of moving a support including the X-ray detector and an X-ray tube in a non-circular arc to move the detector and the tube around the object while varying the distance between the detector and the object.

SUMMARY OF THE INVENTION

When using C-arm based 3D rotational X-ray scanner systems which are not perfectly isocentric, conventional reconstruction methods according to the prior art typically apply non-linear mathematical methods to determine the effective center of rotation. These methods imply the disadvantages that they provide "a solution" but not necessarily the best, that they do not work for CT scans spanning an angular range of 180° or less (such as e.g. for XperCT roll scans, which are part of Philips' XtraVision product) and that the they do not account for the axis of rotation not being perfectly perpendicular to the image acquisition plane of the substantially circular trajectories along which the X-ray tube and detector array are moved when acquiring a set of 2D projection images.

The present invention is thus addressed to the object of facilitating the correction of scanner-based circular ring artifacts which may arise when using a not perfectly isocentric 3D rotational X-ray scanner system due to non-isocentric motion of the X-ray tube and detector array, thus improving the image quality of tomographically reconstructed 3D images which are calculated based on a set of voxel data obtained by combining the image data of a set of 2D projection images which are acquired from a number of distinct projection directions along a substantially circular trajectory around an object of interest to be visualized.

In view of this object, a first exemplary embodiment of the present invention refers to a calibration method for eliminating substantially circular ring artifacts in a set of radiographic 2D projection images which are acquired from a number of distinct projection directions by a not perfectly isocentric 3D rotational X-ray scanner system equipped with at least one X-ray tube and at least one associated X-ray detector diametrically arranged with respect to said X-ray tube.

The proposed calibration method thereby comprises the step of scanning a calibration phantom from each of said projection directions when moving each of said X-ray tube and X-ray detector along a circular trajectory around an object to be visualized and tomographically reconstructed. For each projection direction, the 3D position of the at least one X-ray tube's focal spot and the 3D center position of the associated at least one X-ray detector from the acquired 2D projection images is calculated. After that, the 3D coordinates of the effective center of rotation about which the not perfectly isocentric 3D rotational X-ray scanner system rotates are determined from a set of geometrical calibration data which is obtained as a result of a 3D calibration procedure executed on the basis of the calculated 3D position data.

According to this first exemplary embodiment, it may be foreseen that said 3D calibration procedure is based on a circular regression algorithm which calculates the center position and the radius of a regression circle best fitted to a 2D projection of a substantially circular ring artifact which is obtained when scanning said calibration phantom from each of said projection directions and projecting the resulting substantially circular ring artifact onto the projection plane in which said regression circle lies. This circular regression algorithm may comprise a least squares fit yielding a circle which best fits to a set of points forming a substantially circular ring artifact which indicate the 3D positions obtained by dividing each line connecting the at least one X-ray tube's focal spot position and the center position of the associated at least one X-ray detector according to a given division ratio. This division ratio may be determined for each of said projection directions by the quotient of the distance between the at least one X-ray tube's momentary focal spot position and the current position of the center of rotation for the particular projection angle at the respective image acquisition time and the distance between the momentary center position of said at least one X-ray detector and the current center of rotation for this projection angle at this time instant. The center position of the resulting regression circle calculated by means of the 3D calibration procedure may then be interpreted as the effective center of rotation in the projection plane of the substantially circular ring artifact when reconstructing an object of interest from the acquired set of radiographic 2D projection images.

According to a further refinement of this first exemplary embodiment, it may be foreseen that a vector direction normal to the plane of the resulting regression circle is interpreted as a directional vector of the effective axis of rotation when reconstructing an object of interest from the acquired set of radiographic 2D projection images. This directional vector may thereby be calculated based on a least squares optimization criterion for fitting a set of points, said points consisting of a given number of discrete points at distinct angular positions of the at least one X-ray tube's focal spot on the focal spot trajectory and a corresponding number of discrete points at the diametrically opposite positions of the at least one X-ray detector's center on the detector trajectory for a set of discrete image acquisition times when acquiring said set of radiographic 2D projection images from said number of distinct projection directions, to a regression circle and interpreting a normal vector on the plane of the resulting regression circle as a directional vector of the effective axis of rotation.

The effective center of rotation may then be calculated as a point located between the trajectory plane of the at least one X-ray tube's focal spot and the trajectory plane of the at least one associated X-ray detector's center, wherein said point thereby lies in the direction of said normal vector, namely in a distance to said focus trajectory plane and said detector trajectory plane whose distance ratio is equal to said division ratio.

A second exemplary embodiment of the present invention is directed to a method for tomographically reconstructing an object of interest from a set of radiographic 2D projection images acquired from a number of distinct projection directions by a not perfectly isocentric 3D rotational X-ray scanner system which comprises at least one X-ray tube and at least one associated X-ray detector diametrically arranged with respect to said X-ray tube, wherein said images are acquired when moving said X-ray tube and said X-ray detector along two circular trajectories around said object. According to the present invention, said method may include a calibration method for eliminating substantially circular ring artifacts as set forth above with respect to said first exemplary embodiment.

A third exemplary embodiment of the present invention is dedicated to a C-arm based 3D rotational X-ray scanner system for use in computed tomography which is not perfectly isocentric, wherein said system comprises a calibration unit adapted for performing a calibration method as set forth above with respect to said first exemplary embodiment. In addition thereto, the proposed C-arm system may comprise a reconstruction unit interacting with said calibration unit, wherein said reconstruction unit is adapted for performing a reconstruction method as set forth above with respect to said second exemplary embodiment.

Finally, a fourth exemplary embodiment of the present invention relates to a computer program product for executing a method as set forth above with respect to said first exemplary embodiment when being implemented and running on a calibration unit for calibrating a C-arm based 3D rotational X-ray scanner system as set forth above with respect to said third exemplary embodiment. As an advantageous aspect of the present invention, it may further be provided that said computer program product may comprise a software routine for executing a method as set forth above with respect to said second exemplary embodiment when being implemented and running on a reconstruction unit of a C-arm based 3D rotational X-ray imaging system as set forth with respect to said third exemplary embodiment.

BRIEF DESCRIPTION OF THE DRAWINGS

These and other advantageous aspects of the invention will be elucidated by way of example with respect to the embodiments described hereinafter and with respect to the accompanying drawings. Therein, FIG. 5 shows a flow chart which illustrates a calibration and 3D reconstruction method according to the present invention.

DETAILED DESCRIPTION OF THE PRESENT INVENTION

In the following, the claimed calibration method and C-arm based 3D rotational X-ray imaging system according to the above-described exemplary embodiments of the present invention will be explained in more detail with respect to special refinements and referring to the accompanying drawings.

Figure 1A:
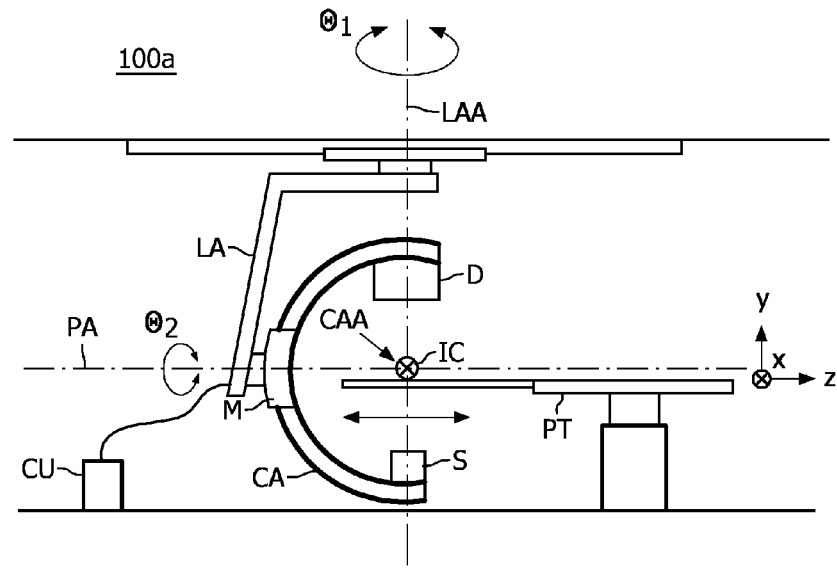
FIG. 1a shows a conventional setup configuration of a mobile C-arm based rotational X-ray scanner system for use in tomographic X-ray imaging as known from the prior art.

In FIG. 1a, a conventional setup configuration of a mobile C-arm based rotational X-ray scanner system 100a for use in tomographic X-ray imaging as known from the relevant prior art (e.g. such as disclosed in US 2002/0168053 A1) is shown. The depicted CT system comprises an X-ray source S and an X-ray detector D arranged at opposite ends of a C-arm CA which is journally mounted so as to be rotatable about a horizontal propeller axis PA and a horizontal C-arm axis CAA perpendicular to said propeller axis by means of a C-arm mount M, thus allowing said X-ray source and X-ray detector to rotate by a rotational angle ($\theta_1$ or $\theta_2$, respectively) about the y- and/or z-axis of a stationary 3D Cartesian coordinate system spanned by the orthogonal coordinate axes x, y and z, wherein the x-axis has the direction of C-arm axis CAA, the y-axis is a vertical axis normal to the plane of the patient table (z-x-plane) and the z-axis has the direction of propeller axis PA. C-arm axis CAA, which points in a direction normal to the plane of drawing (y-z-plane), thereby passes through the isocenter IC of the C-arm assembly. A straight connection line between the focal spot position of X-ray source S and the center position of X-ray detector D intersects propeller axis PA and C-arm axis CAA at the coordinates of isocenter IC. C-arm CA is journaled, by way of an L-arm LA, so as to be rotatable about an L-arm axis LAA which has the direction of the y-axis and intersects propeller axis PA and C-arm axis CAA at the coordinates of isocenter IC. A control unit CU is provided for continuously controlling the operation of at least two motors that are used for moving X-ray source S and X-ray detector D along a specified trajectory around an object of interest which is placed in the area of isocenter IC within a spherical orbit (examination range) covered by C-arm CA when rotating about L-arm axis LAA or propeller axis PA. From FIG. 1a it can easily be taken that C-arm CA with X-ray detector D and X-ray source S can be rotated about C-arm axis CAA while at the same time the C-arm mount M is rotated about the propeller axis PA and projection images of an object of interest to be examined are acquired.

Figure 1B:
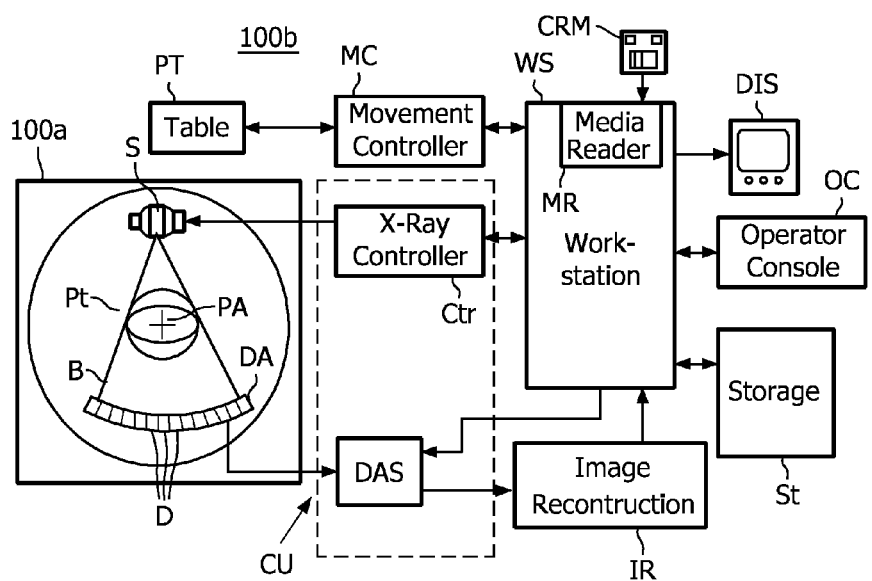
FIG. 1b shows a schematic block diagram which illustrates the signal flow as needed for controlling the operation of the mobile C-arm based rotational X-ray scanner system illustrated in FIG. 1a, FIG. 2 shows a transversal body scan deteriorated by circular ring artifacts generated due to an imperfect aligning of the mechanical components of a mobile C-arm based rotational X-ray scanner system which causes the center of rotation to vary over the rotation angle.

A schematic block diagram 100b which illustrates the signal flow as needed for controlling the operation of the mobile C-arm based rotational X-ray scanner system 100a illustrated in FIG. 1a is shown in FIG. 1b. In the schematic block diagram of FIG. 1b, only a single row of detector elements D is shown (i.e., a detector row). However, a multi-slice detector array such as denoted by reference number DA comprises a plurality of parallel rows of detector elements D such that projection data corresponding to a plurality of quasi-parallel or parallel slices can be acquired simultaneously during a scan. Alternatively, an area detector may be utilized to acquire cone-beam data. Operation of X-ray source S is governed by a control mechanism of CT system 100a which is executed by control unit CU. Control unit CU comprises an X-ray controller Ctr that provides power and timing signals to X-ray source S. A data acquisition system DAS belonging to said control mechanism CU samples analog data from detector elements D and converts the data to digital signals for subsequent processing. An image reconstructor IR receives sampled and digitized X-ray data from data acquisition system DAS and performs high-speed image reconstruction. The reconstructed image is applied as an input to a workstation WS, which stores the image in a mass storage device St. The image reconstructor IR may be specialized hardware residing in workstation WS or a software program executed by this computer.

The workstation WS also receives signals via a user interface or graphical user interface (GUI). Specifically, said computer receives commands and scanning parameters from an operator console OC which in some configurations may include a keyboard and mouse (not shown). An associated display DIS (e.g., a cathode ray source display) allows the operator to observe the reconstructed image and other data from workstation WS. The operator-supplied commands and parameters are used by workstation WS to provide control signals and information to X-ray controller Ctr, data acquisition system DAS and a table motor controller MC (also referred to as "movement controller") in communication with a motorized patient table PT, which controls said patient table so as to accurately position a patient Pt. In some configurations, workstation WS may comprise a storage device MR (also referred to as "media reader"), e.g. a floppy disk drive, CD-ROM drive, DVD drive, magnetic optical disk (MOD) device or any other digital device including a network connecting device such as an Ethernet device for reading instructions and/or data from a computer-readable medium CRM, such as e.g. a floppy disk, a CD-ROM or a DVD.

Figure 2:
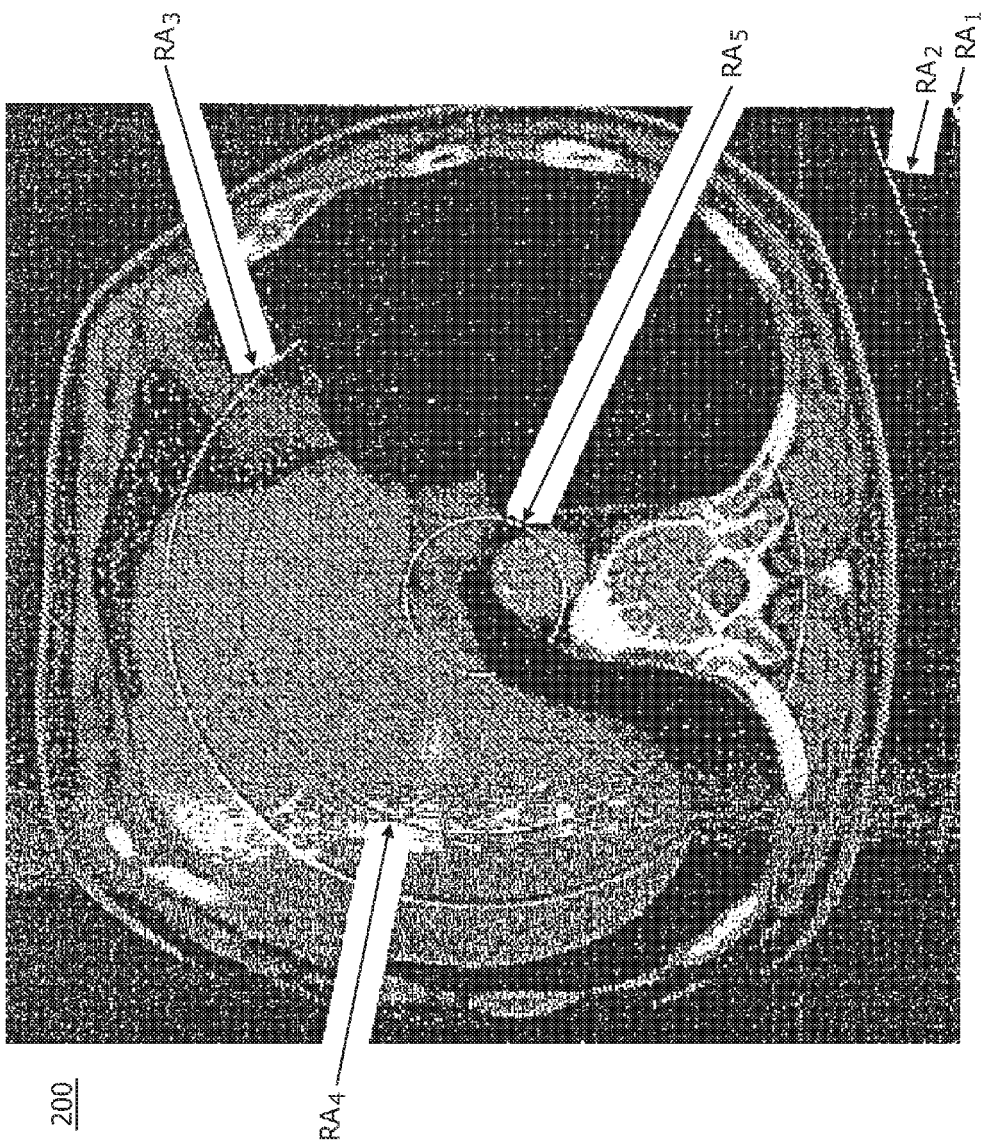

FIG. 2 shows a transversal body scan deteriorated by a number of concentric circular ring artifacts ($RA_1$, $RA_2$, $RA_3$, $RA_4$ and $RA_5$) generated due to an imperfect aligning of the mechanical components of a mobile C-arm based rotational X-ray scanner system which is not perfectly isocentric (to be more precise, due to an imperfect aligning of an X-ray tube's focus and an X-radiation sensitive detector or detector array exposed to and irradiated by the X-ray beams emitted from said X-ray tube), which causes the center of rotation to vary over the rotation angle. Since the axis of rotation may not be perfectly normal to a transversal imaging plane (x-y-plane) spanned by the two orthogonal coordinate axes x and y, the center of rotation may be different for each slice of a three-dimensionally reconstructed object of interest (see FIG. 4c).

Figure 3:
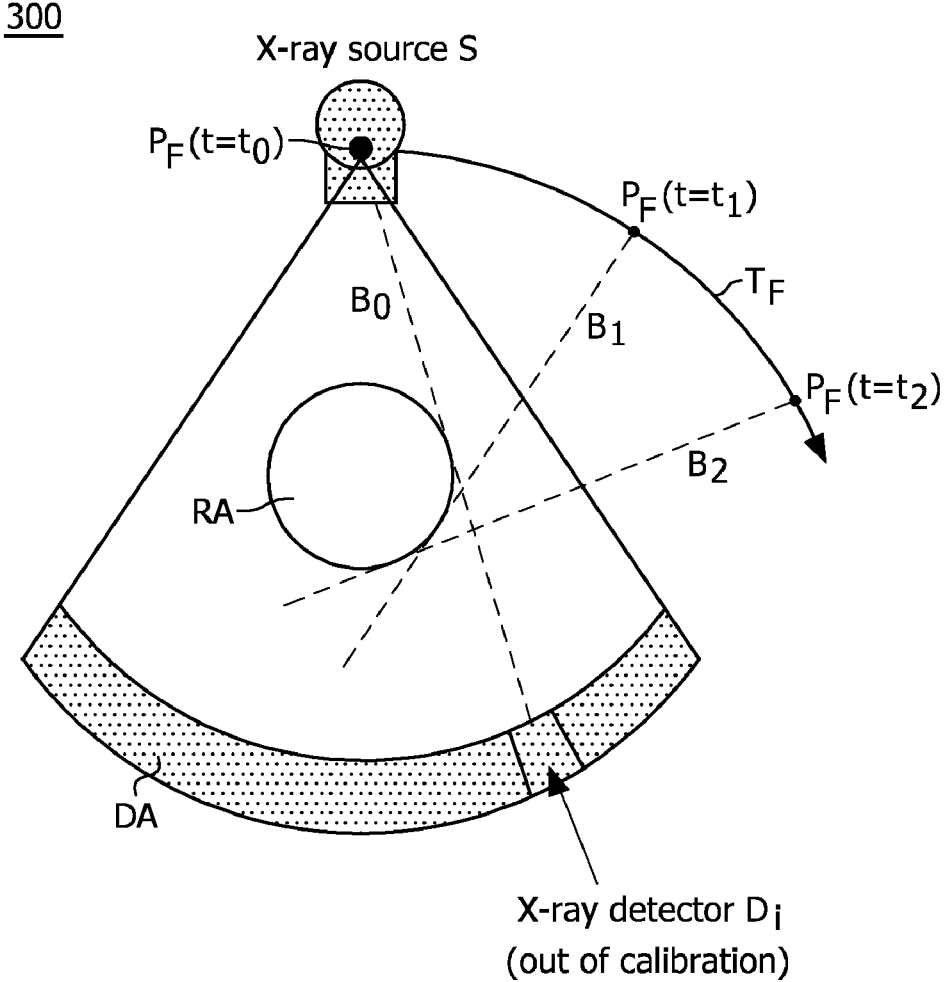
FIG. 3 illustrates the formation of a circular ring artifact during an image acquisition session with a perfectly isocentric third-generation 3D rotational X-ray scanner system which comprises one X-ray detector being out of calibration.

In FIG. 3, a schematic diagram is shown which illustrates the formation of a circular ring artifact RA during an image acquisition session with a perfectly isocentric third-generation 3D rotational X-ray scanner system with a rotating X-ray tube S whose focal spot is moved in an image acquisition plane along a circular trajectory $T_F$ around an object of interest (not shown) and a co-rotated X-radiation sensitive detector array DA oppositely arranged to said X-ray source, wherein one X-ray detector $D_i$ contained in said detector array DA is out of calibration. As already explained above, such a circular ring artifact RA may also arise when three-dimensionally reconstructing an object of interest from the voxel data of a set of 2D projection images which have been acquired by the X-ray tube and X-ray detector of a non-ideal isocentric 3D rotational X-ray scanner system while the X-ray tube's focal spot and the detector center of the X-ray detector are being moved along a not perfectly circular focus trajectory $T_F$ or a not perfectly circular detector trajectory $T_{CD}$, respectively.

Figure 4A:
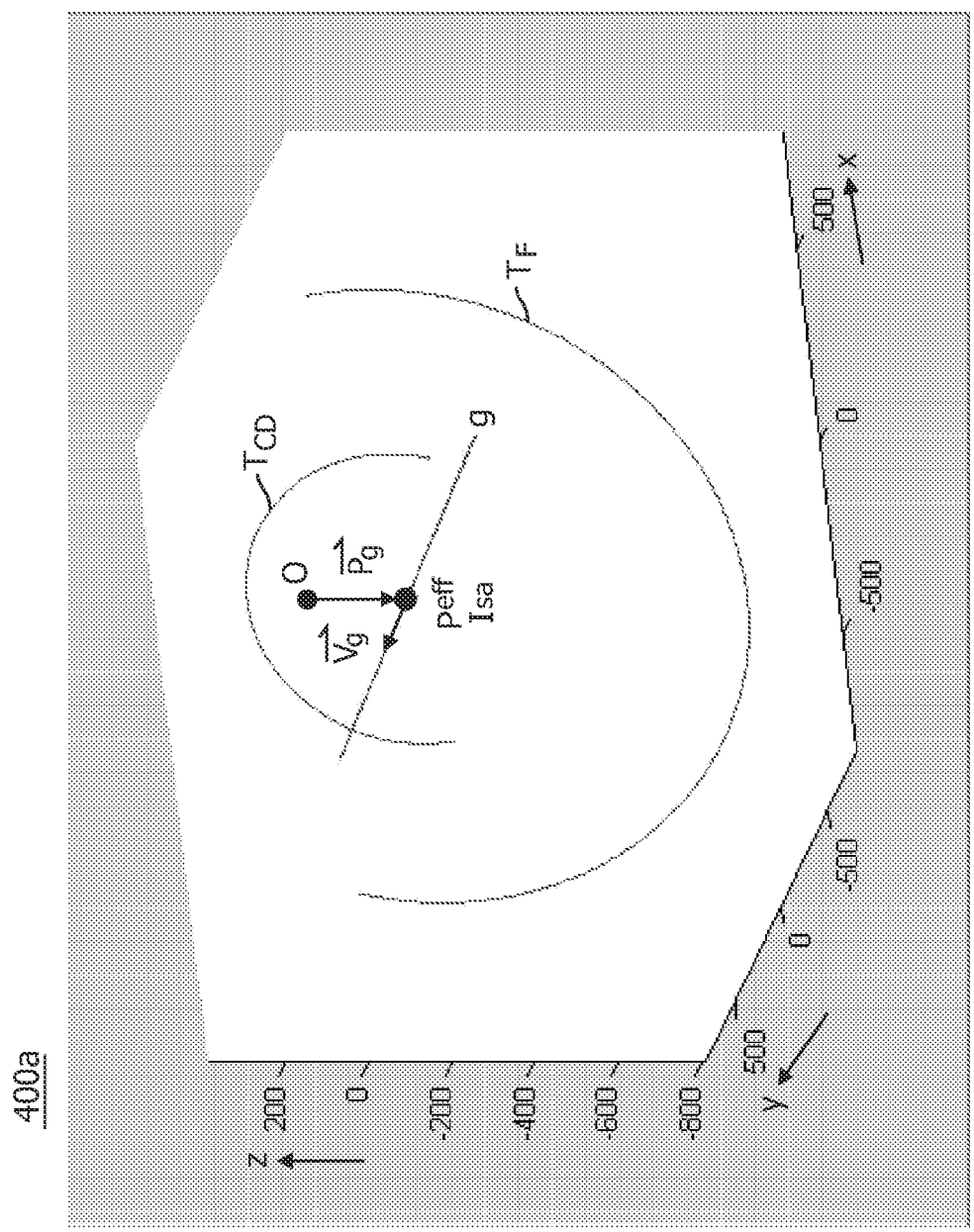
FIG. 4a is a 3D diagram which shows one half of a not perfectly circular trajectory on which the focal spot of a non-ideal isocentric 3D rotational X-ray scanner system's X-ray tube is moved and the corresponding half of a not perfectly circular trajectory on which the center of an X-radiation sensitive detector oppositely arranged to said X-ray tube is moved, said trajectories being determined by using a calibration phantom, as well as the position and angular direction of the corresponding effective center of rotation and effective axis of rotation which are obtained as a result of the calibration method as set forth in the present application.

Referring now to FIG. 4a, a 3D diagram is shown which depicts one half of a not perfectly circular focus trajectory $T_F$ passed by the focal spot of a 3D rotational X-ray scanner system's X-ray tube S and the corresponding half of a not perfectly circular detector trajectory $T_{CD}$ passed by the center of an X-radiation sensitive detector D diametrically arranged with respect to said X-ray tube and being exposed to and irradiated with an X-ray beam emitted from said X-ray tube as determined in the scope of the calibration method as described and claimed in the present application. As described above, said trajectories may be determined in 3D by using a calibration phantom. As a result of the herein described method, the positional vector $\vec{p}_g = OP_{Iso}^{eff}$ of the effective center of rotation $P_{Iso}^{eff}$ (with O being the origin of a stationary 3D Cartesian coordinate system with the three orthogonal coordinate axes x, y and z) and the directional vector 17, of the effective axis of rotation (or "effective isocenter") are obtained, wherein the latter is depicted as straight line g: $=\{\vec{x}\in R^3 | \vec{x}=\vec{p}_g+\mu\cdot\vec{v}_g \text{ with } \mu\in R\}$ in a 3D vector space which is spanned by these coordinate axes.

Figure 4B:
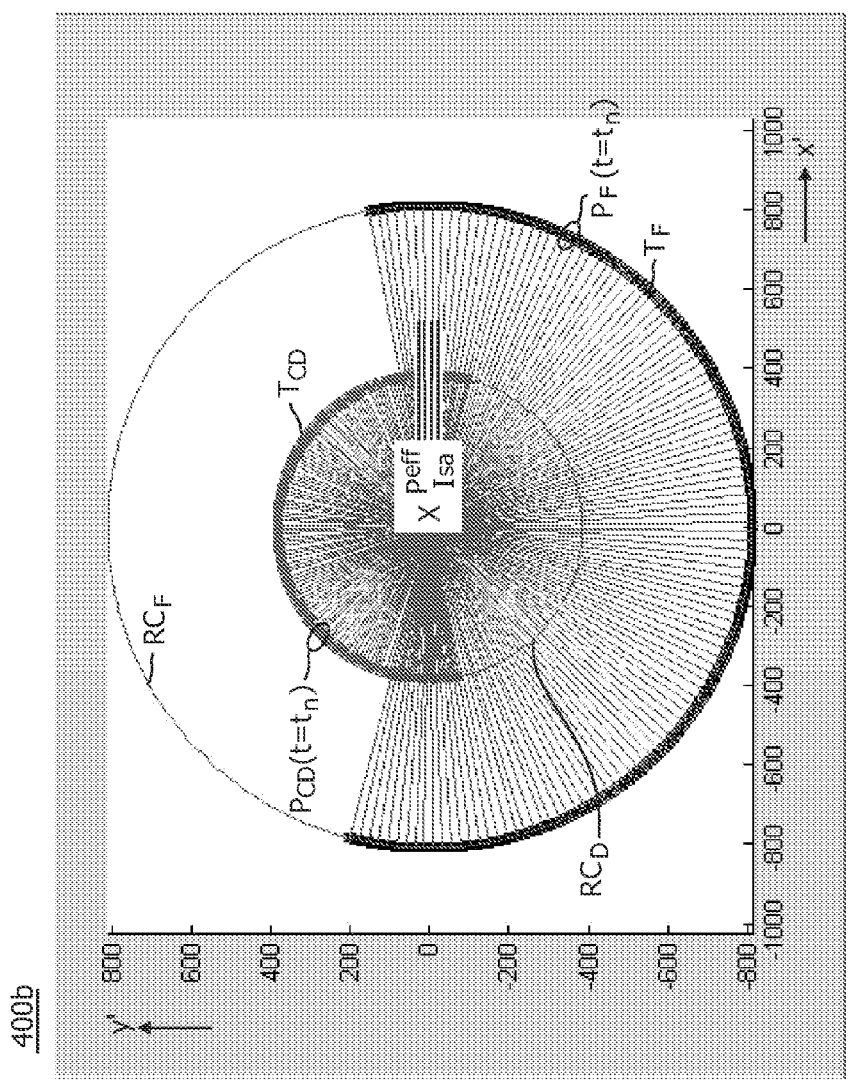
FIG. 4b is a 2D diagram which shows, projected into a 2D projection plane, a set of points forming the focus trajectory (half circle with large radius printed with bold line type) and a further set of points forming the detector trajectory (half circle with small radius printed with bold line type) as well as corresponding regression circles best fitted to the respective trajectories according to a least squares optimization criterion.

In FIG. 4b, a 2D diagram is depicted which shows, projected into a 2D projection plane (x'-y'-plane) as given by the focus trajectory plane (here exemplarily given as being coplanar to the detector trajectory plane), a set of points forming said focus trajectory $T_F$ (half circle with large radius printed with bold line type) and a further set of points forming said detector trajectory $T_{CD}$ (half circle with small radius printed with bold line type). Furthermore, a corresponding regression circle $RC_F$ best fitted to the focus trajectory and a corresponding regression circle $RC_D$ best fitted to the detector trajectory according to a least squares optimization criterion are depicted in this 2D diagram. Points $P_F(t=t_n)$ and $P_{CD}(t=t_n)$ denote the momentary positions of the X-ray tube's focal spot and the center of said X-radiation sensitive detector D at discrete image acquisition time $t=t_n$ (with $t_n=t_0+n\Delta t$ and $n\in\{0, 1, 2, \ldots, N\}$, wherein $t_0$ is the starting time for an image acquisition session and $\Delta t$ denotes the scan interval between an acquisition of two subsequent 2D projection images from two adjacent projection directions when rotating X-ray tube S and X-ray detector D of the 3D rotational C-arm scanner system around an object of interest to be tomographically reconstructed and visualized).

Figure 4C:
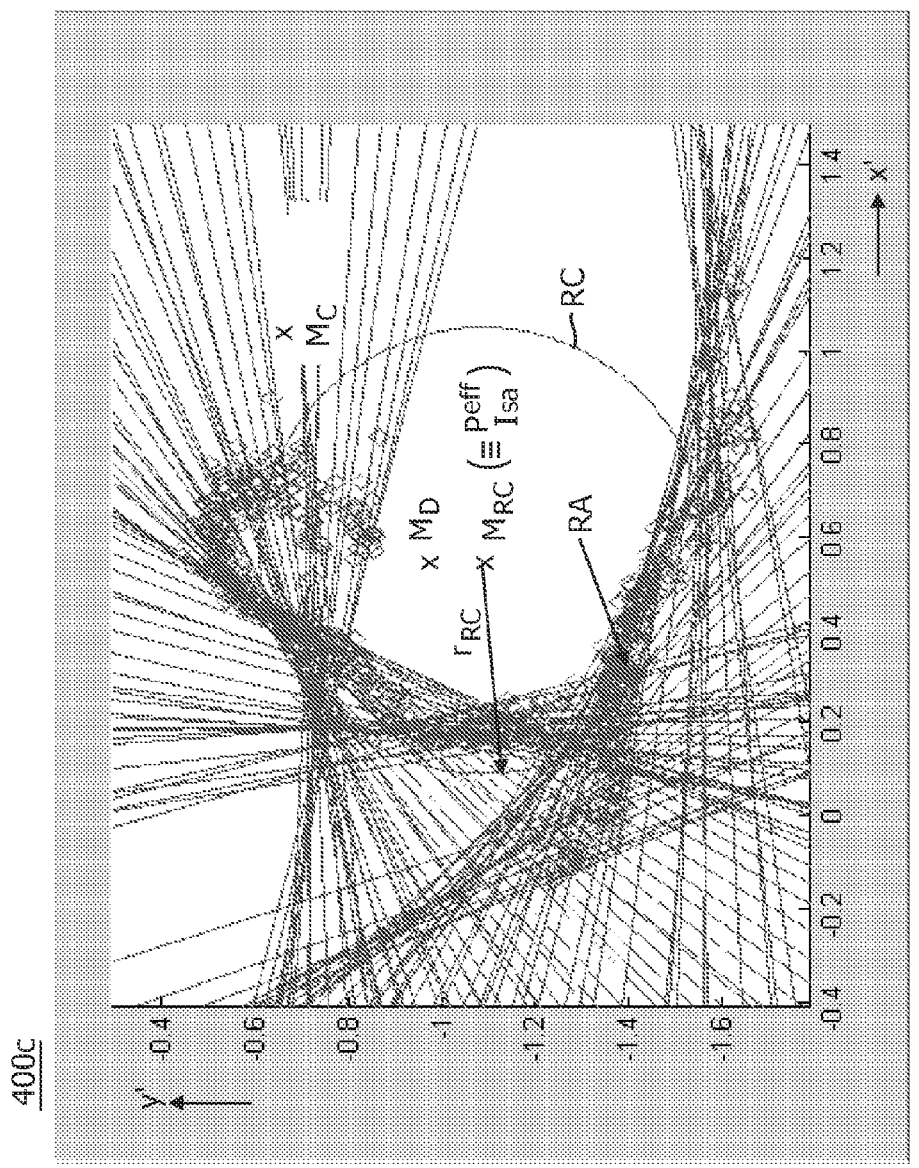
FIG. 4c shows a zoomed version of the 2D diagram in FIG. 4b in an area close to the calculated effective center of rotation, thereby showing, projected into the aforementioned 2D projection plane, a set of points forming an artifact that slightly resembles a circle which are fitted with a regression circle according to a least squares optimization criterion.

FIG. 4c shows a zoomed version of the 2D diagram in FIG. 4b in an area close to the calculated effective center of rotation $P_{Iso}^{eff}$, thereby showing, projected into the focus trajectory plane (x'-y'-plane), a set of points forming an artifact that slightly resembles a circle which are fitted with a regression circle RC according to a least squares optimization criterion. For example, a method as described in published document "Study of undeterministic methods for data separation in physics. Technical report No. 903" (Institute of Computer Science, Academy of Sciences of the Czech Republic. December 2003; ftp://ftp.cs.cas.cz/pub/reports/v903-03.pdf) by M. Mina and F. Hakl can be used for linearizing this problem. As a result of this method, the center $M_{RC}$ and radius $r_{RC}$ of said regression circle RC are obtained, wherein the center coordinates can be interpreted as the effective center of rotation ("effective isocenter") of the 3D rotational C-arm scanner system. According to the invention as disclosed in the present application, said set of points is obtained by drawing a straight connection line from the X-ray focus to the detector center for each projection direction (and thus for each image acquisition time $t_n$) and dividing each line connecting the X-ray tube's focal spot position $P_F(t=t_n)$ and the center position $P_{CD}(t=t_n)$ of the X-ray detector according to a division ratio $\chi_n$ which is determined for each projection direction by the quotient of the distance between said X-ray tube's momentary focal spot position $P_F(t=t_n)$ and the current position of the center of rotation for the respective projection angle at time $t=t_n$ and the distance between the momentary center position $P_{CD}(t=t_n)$ of said X-ray detector and the current center of rotation for this projection angle at this time instant. The center $M_{RC}$ of the resulting regression circle RC, which corresponds to the centroid position of the substantially circular ring artifact, can thus be interpreted as the C-arm system's effective center of rotation $P_{Iso}^{eff}$. As can easily be taken from FIG. 4c, the centers of the fits to all focus positions and detector positions (in FIG. 4c referred to as "focus centroid position" and "detector centroid position", given by the centers $M_F$ and $M_D$ of focus regression circle $RC_F$ and detector regression circle $RC_D$, respectively) may not necessarily coincide with the effective center of rotation $P_1$ as given by the center position $M_{RC}$ of calculated regression circle RC. It can also be derived from FIG. 4c that calculated regression circles $RC_F$ and $RC_D$ may not necessarily be concentric as their centers $M_F$ and $M_D$ are depicted as separate points which do not coincide.

It is to be noted that the above-described method only refers to a least squares fit of said set of points forming said artifact, projected into the focus trajectory plane, to a regression circle which lies in this plane. In practice, however, due to mechanical shearing forces and bending moments applied to the ends of the C-arm CA where the X-ray tube and X-ray detector are mounted and/or due to an imperfect alignment of these system components, the true effective axis of rotation (here exemplarily given by the propeller axis PA) is not perfectly normal to an exactly vertical image acquisition plane (x-y-plane) as required for accurately performing a transversal body scan. Therefore, one more step has to be performed. According to a further refinement of the procedure as described above, the proposed method comprises a linear squares fit of a set points consisting of the discrete focal spot positions $P_F(t=t_n)$ on the focus trajectory $T_F$ and the corresponding discrete detection center positions $P_{CD}(t=t_n)$ on the detector trajectory $T_{CD}$ to a regression circle in 3D. The obtained regression circle lies in a plane which can then be interpreted as constituting the true effective plane of rotation E, in the following also referred to as x"-y"-plane (not shown). A vector $\vec{n}_E$ normal to this plane whose 3D coordinates are obtained as an output of this method, in particular a normal vector $\vec{n}_{E0}$ that is normalized to length one, is then calculated and interpreted as pointing in the direction of the true effective axis of rotation. This hence differs from the situation as depicted in FIG. 4c where the angular direction of the effective axis of rotation is that of a normal vector on the focus trajectory plane or co-planar detector trajectory plane, respectively.

Said refinement procedure further foresees that the true effective center of rotation, in the following referred to as $P_{Iso}^{effi}$, can then be found as a point located between the focus trajectory plane and the detector trajectory plane which is lying in the direction of normalized normal vector $\vec{n}_{E0}$, namely in a distance to said focus trajectory plane and said detector trajectory plane whose distance ratio is equal to said division ratio $\chi_n$. The coordinates of $P_{Iso}^{effi}$ can thus be found by a projection of regression circle RC's center $M_{RC}$ on the x"-y"-plane.

A flow chart for illustrating a calibration and 3D reconstruction method according to the present invention is shown in FIG. 5.

The method begins with an inquiry for checking (S1) whether a control command for initiating a new image acquisition session (such as e.g. a power-on signal) has already been received. As long as this is not the case, the procedure is continued in a loop with step S1 after a given delay time. After having received such a switching command, a calibration phantom is scanned (S2) from each of said projection directions when moving each of said X-ray tube and X-ray detector along a circular trajectory around an object to be visualized and tomographically reconstructed. For each projection direction, the 3D position of the at least one X-ray tube's focal spot and the 3D center position of the associated at least one X-ray detector (D) from the acquired 2D projection images are calculated (S3). After that, the 3D coordinates of the effective center of rotation about which the not perfectly isocentric 3D rotational X-ray scanner system rotates as well as the directional vector of the effective axis of rotation are determined (S5, S5') from a set of geometrical calibration data which is obtained as a result of a 3D calibration procedure (S4) executed on the basis of the calculated 3D position data. When receiving (S6) a switching command for terminating the running image acquisition session (such as e.g. a power-off signal), the acquired 2D projection images are subjected to a 3D reconstruction procedure (S7) which uses the calculated coordinates of the effective center of rotation and/or the calculated directional vector of the effective axis of rotation for correspondingly correcting substantially circular ring artifacts which otherwise would arise due to said X-ray tube's focal spot and said X-ray detector center moving on not perfectly isocentric focus and detector trajectories, respectively, while rotating around an object of interest during said image acquisition session. Otherwise, the procedure is continued again with step S6 after expiry of a given delay time.

Applications of the Present Invention

The present invention and the above exemplary embodiments may be used in the scope of not perfectly isocentric 3D rotational X-ray imaging systems for use in computed tomography and, more precisely, in the scope of a 3D reconstruction application using a phantom-based 3D calibration procedure for performing a ring artifact correction algorithm such as performed by the XperCT ring artifact correction module of XtraVision release 6.2.2. The proposed method thereby proved to work very well for both propeller scans over an angular range of 200° and roll scans over an angular range of 180°.

While the present invention has been illustrated and described in detail in the drawings and in the foregoing description, such illustration and description are to be considered illustrative or exemplary and not restrictive, which means that the invention is not limited to the disclosed embodiments. Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures can not be used to advantage. A computer program may be stored or distributed on a suitable medium, such as e.g. an optical storage medium or a solid-state medium supplied together with or as part of other hardware, but may also be distributed in other forms, such as e.g. via the Internet or other wired or wireless telecommunication systems. Any reference signs in the claims should not be construed as limiting the scope of the invention.

The invention claimed is:

1. A calibration method for eliminating substantially circular ring artifacts ($RA$, $RA_1$, $RA_2$, $RA_3$, $RA_4$, $RA_5$) in a set of radiographic 2D projection images which are acquired from a number of distinct projection directions by a not perfectly isocentric 3D rotational X-ray scanner system equipped with at least one X-ray tube (S) and at least one associated X-ray detector (D) diametrically arranged with respect to said X-ray tube (S), wherein not perfectly isocentric corresponds to the 3D rotational X-ray scanner system having an imperfect aligning of (i) a focus of the at least one X-ray tube (S) and (ii) the at least one associated X-ray detector (D) exposed to and irradiated by X-ray beams emitted from the at least one X-ray tube (S), which causes a center of rotation to vary over a rotation angle for the distinct projection directions, said calibration method comprising the steps of scanning (S2) a calibration phantom from each of said projection directions when moving each of said X-ray tube (S) and X-ray detector (D) along a circular trajectory ($T_F$, $T_{CD}$) around an object to be visualized and tomographically reconstructed, for each projection direction, calculating (S3) the 3D position ($P_F$) of the at least one X-ray tube's focal spot and the 3D center position ($P_{CD}$) of the associated at least one X-ray detector (D) from the acquired 2D projection images and determining (S5) the 3D coordinates of the effective center of rotation ($M_{RC}$, $P_{Iso}^{eff}$ or $P_{Iso}^{eff}$) about which the not perfectly isocentric 3D rotational X-ray scanner system rotates from a set of geometrical calibration data which is obtained as a result of a 3D calibration procedure (S4) executed on the basis of the calculated 3D position data.

2. The calibration method according to claim 1, wherein said 3D calibration procedure (S4) is based on a circular regression algorithm which calculates the center position ($M_{RC}$, $P_{Iso}^{eff}$) and the radius ($r_{RC}$) of a regression circle (RC) best fitted to a 2D projection of a substantially circular ring artifact (RA) which is obtained when scanning said calibration phantom from each of said projection directions and projecting the resulting substantially circular ring artifact (RA) onto the projection plane in which said regression circle (RC) lies.

3. The calibration method according to claim 2, wherein said circular regression algorithm comprises a least squares fit yielding a circle which best fits to a set of points ($\diamond$) forming a substantially circular ring artifact (RA) which indicate the 3D positions obtained by dividing each line connecting the at least one X-ray tube's focal spot position ($P_F$) and the center position ($P_{CD}$) of the associated at least one X-ray detector (D) according to a given division ratio ($\chi_n$).

4. The calibration method according to claim 3, wherein said division ratio ($\chi_n$) is determined for each of said projection directions by the quotient of the distance between the at least one X-ray tube's momentary focal spot position ($P_F(t=t_n)$) and the current position of the center of rotation for the particular projection angle at the respective image acquisition time ($t_n$) and the distance between the momentary center position ($P_{CD}(t=t_n)$) of said at least one X-ray detector (D) and the current center of rotation for this projection angle at this time instant ($t_n$).

5. The calibration method according to claim 4, wherein the center position ($M_{RC}$) of the resulting regression circle (RC) calculated by means of the 3D calibration procedure is interpreted as the effective center of rotation ($P_{Iso}^{eff}$) in the projection plane of the substantially circular ring artifact (RA) when reconstructing an object of interest from the acquired set of radiographic 2D projection images.

6. The calibration method according to claim 4, wherein a vector direction normal to the plane of the resulting regression circle (RC) is interpreted as a directional vector of the effective axis of rotation (LAA or PA) when reconstructing an object of interest from the acquired set of radiographic 2D projection images.

7. The calibration method according to claim 3, wherein the center position ($M_{RC}$) of the resulting regression circle (RC) calculated by means of the 3D calibration procedure is interpreted as the effective center of rotation ($P_{Iso}^{eff}$) in the projection plane of the substantially circular ring artifact (RA) when reconstructing an object of interest from the acquired set of radiographic 2D projection images.

8. The calibration method according to claim 3, wherein a vector direction normal to the plane of the resulting regression circle (RC) is interpreted as a directional vector of the effective axis of rotation (LAA or PA) when reconstructing an object of interest from the acquired set of radiographic 2D projection images.

9. The calibration method according to claim 2, wherein the center position ($M_{RC}$) of the resulting regression circle (RC) calculated by means of the 3D calibration procedure is interpreted as the effective center of rotation ($P_{Iso}^{eff}$) in the projection plane of the substantially circular ring artifact (RA) when reconstructing an object of interest from the acquired set of radiographic 2D projection images.

10. The calibration method according to claim 2, wherein a vector direction normal to the plane of the resulting regression circle (RC) is interpreted as a directional vector of the effective axis of rotation (LAA or PA) when reconstructing an object of interest from the acquired set of radiographic 2D projection images.

11. The calibration method according to claim 1, wherein the directional vector of the effective axis of rotation (LAA or PA) is calculated based on a least squares optimization criterion for fitting a set of points, said points consisting of a given number of discrete points ($P_F$ ($t=t_n$)) at distinct angular positions of the at least one X-ray tube's focal spot on the focal spot trajectory ($T_F$) and a corresponding number of discrete points ($P_{CD}$ ($t=t_n$)) at the diametrically opposite positions of the at least one X-ray detector's center on the detector trajectory ($T_{CD}$) for a set of discrete image acquisition times ($t_n$) when acquiring said set of radiographic 2D projection images from said number of distinct projection directions, to a regression circle (RC) and interpreting a normal vector ($\vec{n}_E$) on the plane (E) of the resulting regression circle as a directional vector of the effective axis of rotation (LAA or PA).

12. The calibration method according to claim 11, wherein the effective center of rotation ($P_{Iso}^{eff}$) is calculated as a point located between the trajectory plane of the at least one X-ray tube's focal spot and the trajectory plane of the at least one associated X-ray detector's center, said point lying in the direction of said normal vector ($\vec{n}_E$), namely in a distance to said focus trajectory plane and said detector trajectory plane whose distance ratio is equal to said division ratio ($\chi_n$).

13. A method for tomographically reconstructing an object of interest from a set of radiographic 2D projection images acquired from a number of distinct projection directions by a not perfectly isocentric 3D rotational X-ray scanner system comprising at least one X-ray tube (S) and at least one associated X-ray detector (D) diametrically arranged with respect to said X-ray tube (S), wherein not perfectly isocentric corresponds to the 3D rotational X-ray scanner system having an imperfect aligning of (i) a focus of the at least one X-ray tube (S) and (ii) the at least one associated X-ray detector (D) exposed to and irradiated by X-ray beams emitted from the at least one X-ray tube (S), which causes a center of rotation to vary over a rotation angle for the distinct projection directions, said images being acquired when moving said X-ray tube (S) and said X-ray detector (D) along two circular trajectories around said object, wherein said method includes a calibration method for eliminating substantially circular ring artifacts ($RA_1$, $RA_2$, $RA_3$, $RA_4$, $RA_5$) according to claim 1.

14. A C-arm based 3D rotational X-ray scanner system for use in computed tomography which is not perfectly isocentric, wherein not perfectly isocentric corresponds to the C-arm based 3D rotational X-ray scanner system having an imperfect aligning of (i) a focus of at least one X-ray tube (S) and (ii) at least one associated X-ray detector (D) exposed to and irradiated by X-ray beams emitted from the at least one X-ray tube (S), which causes a center of rotation to vary over a rotation angle for distinct projection directions, comprising a calibration unit adapted for performing a calibration method as set forth in claim 1.

15. A C-arm based 3D rotational X-ray scanner system according to claim 14, comprising a reconstruction unit interacting with said calibration unit.

16. A non-transitory computer-readable medium embodied with a computer program for executing a method according to claim 1 when being implemented and running on a calibration unit for calibrating a C-arm.

17. A non-transitory computer-readable medium embodied with a computer program according to claim 16 being implemented and running on a reconstruction unit of a C-arm based 3D rotational X-ray scanner system.

18. A C-arm based 3D rotational X-ray scanner system for use in computed tomography which is not perfectly isocentric, wherein not perfectly isocentric corresponds to the C-arm based 3D rotational X-ray scanner system having an imperfect aligning of (i) a focus of at least one X-ray tube (S) and (ii) at least one associated X-ray detector (D) exposed to and irradiated by X-ray beams emitted from the at least one X-ray tube (S), which causes a center of rotation to vary over a rotation angle for distinct projection directions, comprising a calibration unit adapted for performing a calibration method as set forth in claim 2.

19. A C-arm based 3D rotational X-ray scanner system for use in computed tomography which is not perfectly isocentric, wherein not perfectly isocentric corresponds to the C-arm based 3D rotational X-ray scanner system having an imperfect aligning of (i) a focus of at least one X-ray tube (S) and (ii) at least one associated X-ray detector (D) exposed to and irradiated by X-ray beams emitted from the at least one X-ray tube (S), which causes a center of rotation to vary over a rotation angle for distinct projection directions, comprising a calibration unit adapted for performing a calibration method as set forth in claim 3.

20. A C-arm based 3D rotational X-ray scanner system for use in computed tomography which is not perfectly isocentric, wherein not perfectly isocentric corresponds to the C-arm based 3D rotational X-ray scanner system having an imperfect aligning of (i) a focus of at least one X-ray tube (S) and (ii) at least one associated X-ray detector (D) exposed to and irradiated by X-ray beams emitted from the at least one X-ray tube (S), which causes a center of rotation to vary over a rotation angle for distinct projection directions, comprising a calibration unit adapted for performing a calibration method as set forth in claim 4.

* * * * *